(12) United States Patent
Chao

(10) Patent No.: US 6,833,001 B1
(45) Date of Patent: Dec. 21, 2004

(54) CONTROLLABLE TOURNIQUET

(76) Inventor: Richard C. C. Chao, 4F, No. 35-3, Lane 165, Sec. 1, Hsin-Sheng S. Rd., Taipei (TW)

(*) Notice: Subject to any disclaimer, the term of this patent is extended or adjusted under 35 U.S.C. 154(b) by 0 days.

(21) Appl. No.: 10/702,554

(22) Filed: Nov. 7, 2003

(51) Int. Cl.⁷ .................................. A61B 17/00
(52) U.S. Cl. ........................................ 606/203
(58) Field of Search ................. 606/203, 202, 606/201; 600/490, 498, 499; 128/681

(56) References Cited

U.S. PATENT DOCUMENTS 4,102,343 A * 7/1978 Schneider .................. 606/203
4,125,115 A * 11/1978 Mayo et al. ................ 606/203
6,746,470 B2 * 6/2004 McEwen et al. ........... 606/202

* cited by examiner

Primary Examiner—Kevin T. Truong
(74) Attorney, Agent, or Firm—Birch, Stewart, Kolasch & Birch, LLP

(57) ABSTRACT

A controllable tourniquet disclosed in this invention mainly improves the finger pressing component of the tourniquet and the effect of the tourniquet on stopping the bleeding. Such tourniquet comprises an elastic bandage, a latch, and a finger pressing component; wherein the latch is coupled to each end of the elastic bandage, and the finger pressing component is disposed in the middle of the elastic bandage. The finger pressing component can be used to adjust the tightness of the finger pressing bandage to avoid causing any discomfort to the patient, and improve the partial pressurization effect on the tourniquet.

5 Claims, 6 Drawing Sheets

US 6,833,001 B1

CONTROLLABLE TOURNIQUET

FIELD OF THE INVENTION

The present invention relates to a tourniquet, more particularly to a controllable tourniquet that improves the finger pressing components to reduce the patient's discomfort while maintaining the effect of a tourniquet.

BACKGROUND OF THE INVENTION

The tourniquet invented by Johann von Esmarch in 1886 was at first a rubber bandage, primarily used for controlling the bleeding due to the rupture of larger arteries when other stanching methods do not work effectively. The tourniquet should be tied at the position above the bleeding wound of the limbs (just to the extent that the bleeding can be stopped). Lift the wounded limb up for several minutes and place a towel or any other soft tissue onto the tying position to prevent causing abrasion to the tissue. After the tourniquet is applied, the blood circulation of the tissue below the tying position will be stopped. Once the blood circulation is stopped for a long time, hypoxia and necrosis will occur. Therefore, it is inappropriate to tie a tourniquet too long, and it is necessary to release the tourniquet for 30 seconds to one minute once every half an hour and allow the blood to circulate. Therefore, it is necessary to clearly label the appropriate tying time on the tourniquet. The user can then refer to this information to release the tourniquet for necessary treatment.

Besides the first-aid application for stopping the bleeding, a tourniquet can also be used for intravenous injection or blood drawing, in which the tourniquet is applied to the injecting position of the upper limb, so that the unobvious vein can show up under the skin. The vein at the injecting position below the tourniquet is where the blood flows back to the heart, and is deformed by an external pressure of the tourniquet. The cross-sectional area of the vein is reduced; the blood circulation is blocked; the pressure of the vein at that place is increased; and the vein is expanded partially. Therefore, the vein can show up under the skin.

When a tourniquet is used to assist injection, the traditional tourniquet which is a slim circular rubber tube is usually used. In general, the circular rubber tube is stretched to a fixed position for its application. The stretching process also involves a tugging action on the skin which will discomfort the patient. Furthermore, when the tourniquet is released, it usually causes the syringe needle to puncture and give more pain to the patient. After the injection of blood drawing is completed, a piece of cotton for stopping the bleeding is generally used to press the injecting position after the syringe is withdrawn. Such arrangement will create a situation that medical staffs may have a chance to contact the patient's blood, and increase the risk of being infected. Therefore, the inventor of this invention disclosed a controllable tourniquet, and proposed a solution to overcome the shortcomings of the traditional circular rubber tube being tugged on the skin and the syringe needle being punctured deep inside the skin. In FIG. 1, the tourniquet of the present invention comprises a flat long elastic bandage 1, a fine-tune latch 2, and a finger pressing component 3. The fine-tune latch 2 is used to adjust the tightness of the elastic bandage 1, and the finger pressing component 3 is pressed to exert pressure to the tourniquet, so that the medical staff can use the finger pressing component 3 to press the injecting position for stopping the bleeding, and avoid touching the patient's skin and blood. By replacing the finger pressing component 3, the tourniquet can be used for different patients. However, after the invention was invented for a while, the inventor found that there are more issues, which include the operation of the fine-tune latch still having the tugging action on the skin and discomforting the patient. There is a problem about the design of the finger pressing component; when it is in use, an external force must be applied to the finger pressing component in order to accomplish the effect of stopping the bleeding. In general, it takes about 30 to 60 minutes for the coagulation of the blood of a regular patient. Due to the abnormal metabolism of the hematoblasts in the blood, it generally takes longer time for the blood coagulation of an irregular patient such as a hemophiliac or a patient with problem of liver function. Therefore, the long time pressing on the finger pressing component 3 creates an issue to medical staffs as well as patients.

SUMMARY OF THE INVENTION

The primary objective of the present invention is to improve the design of the finger pressing component, so that when the tourniquet is pressurized to stop the bleeding for a long time, the tourniquet can be used for fixing itself in a position without the need of pressurizing manually.

The secondary objective of the present invention is to avoid the tugging action on the skin and reduce discomfort to the patient when the tourniquet is adjusted.

The present invention comprises a finger pressing component, a horizontally adjustable fixture disposed respectively on both ends of the finger pressing component, a knob disposed in the middle of the finger pressing component; wherein a vertical movement caused by the vertical rotation of the knob exerts pressure to the finger pressing component, and the knob will not be in direct contact with the skin. Therefore, when the knob is rotated, it will not have a tugging action on the skin; when the tourniquet is fixed, it will not discomfort the patient. The fixture on both ends of the finger pressing component can make a horizontal adjustment, so that when the tourniquet is stretched to a fixed position, the fixtures on both sides of the finger pressing component can make a slight adjustment by means of the horizontal adjustment.

DETAILED DESCRIPTION OF THE PREFERRED EMBODIMENTS

To make it easier for our examiner to understand the objective of the invention, its structure, innovative features, and performance, we use a preferred embodiment together with the attached drawings for the detailed description of the invention.

Figure 1:
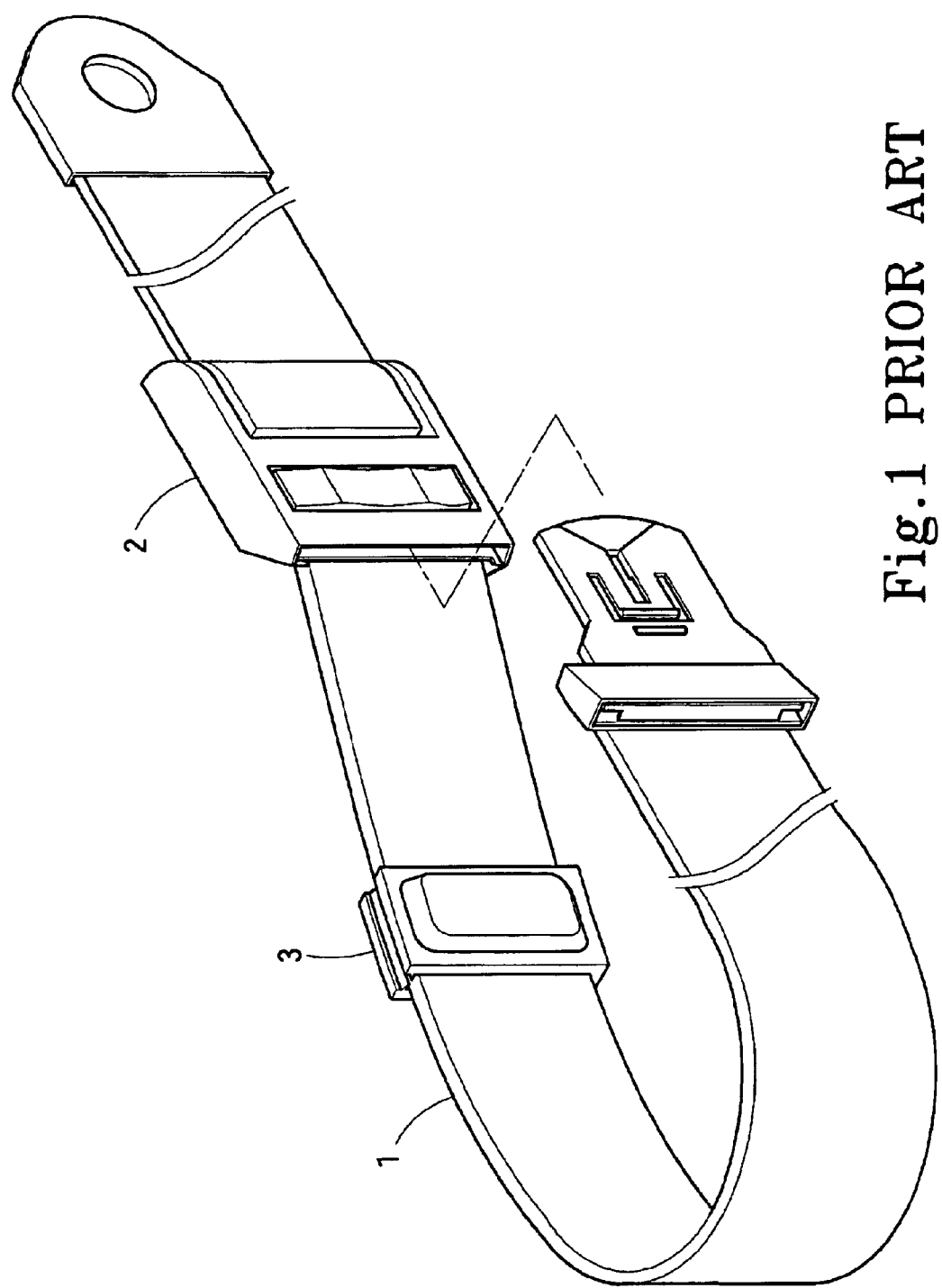
FIG. 1 is a perspective diagram of a prior-art tourniquet.
Figure 2:
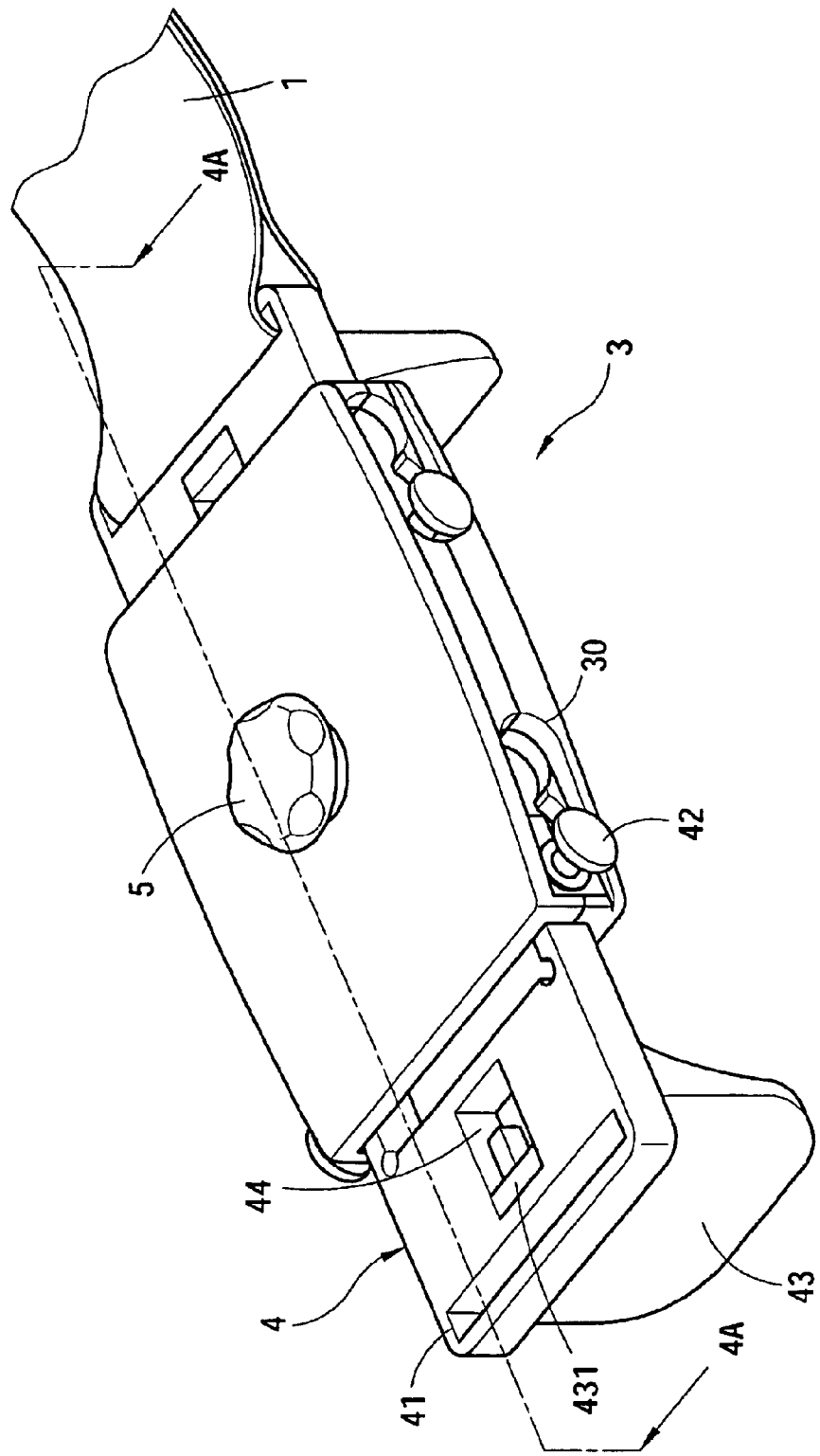
FIG. 2 is a perspective diagram of the appearance of a preferred embodiment of the present invention.

Please refer to FIG. 2 for the illustrative diagram of the appearance of a preferred embodiment of the present invention. The controllable tourniquet in accordance with the invention comprises a finger pressing component 3, a fixture 4 respectively disposed on both ends of the finger pressing component 3, and a rear end 41 of the fixture 4 is coupled to an elastic bandage 1; a plurality of grooves 30 disposed on both sides of the finger pressing component 3 for moving and adjusting a pivotal coupling end 42 of the fixture 4 in the groove 30. When it is necessary to adjust the pivotal coupling end 42, both ends of the pivotal coupling ends 42 are pulled out, so that the pivotal coupling end 42 can be moved horizontally in the groove 30. When the pivotal coupling end 42 is moved to a fixed position, the pivotal coupling end 42 is pushed back and coupled with the groove 30. The fixture 4 has a square latch groove 44 coupled with a latch section 431 of an oval plate 43. When the latch section 431 of the oval plate 43 is in square latch groove 44 of the fixture 4, it is in an adjustable status. The oval plate 43 is used to fix the limb in a position, and thus the distance between the fixture 4 on both sides and the oval plate 43 can be adjusted according to the size of the patient's limb.

Figure 3:
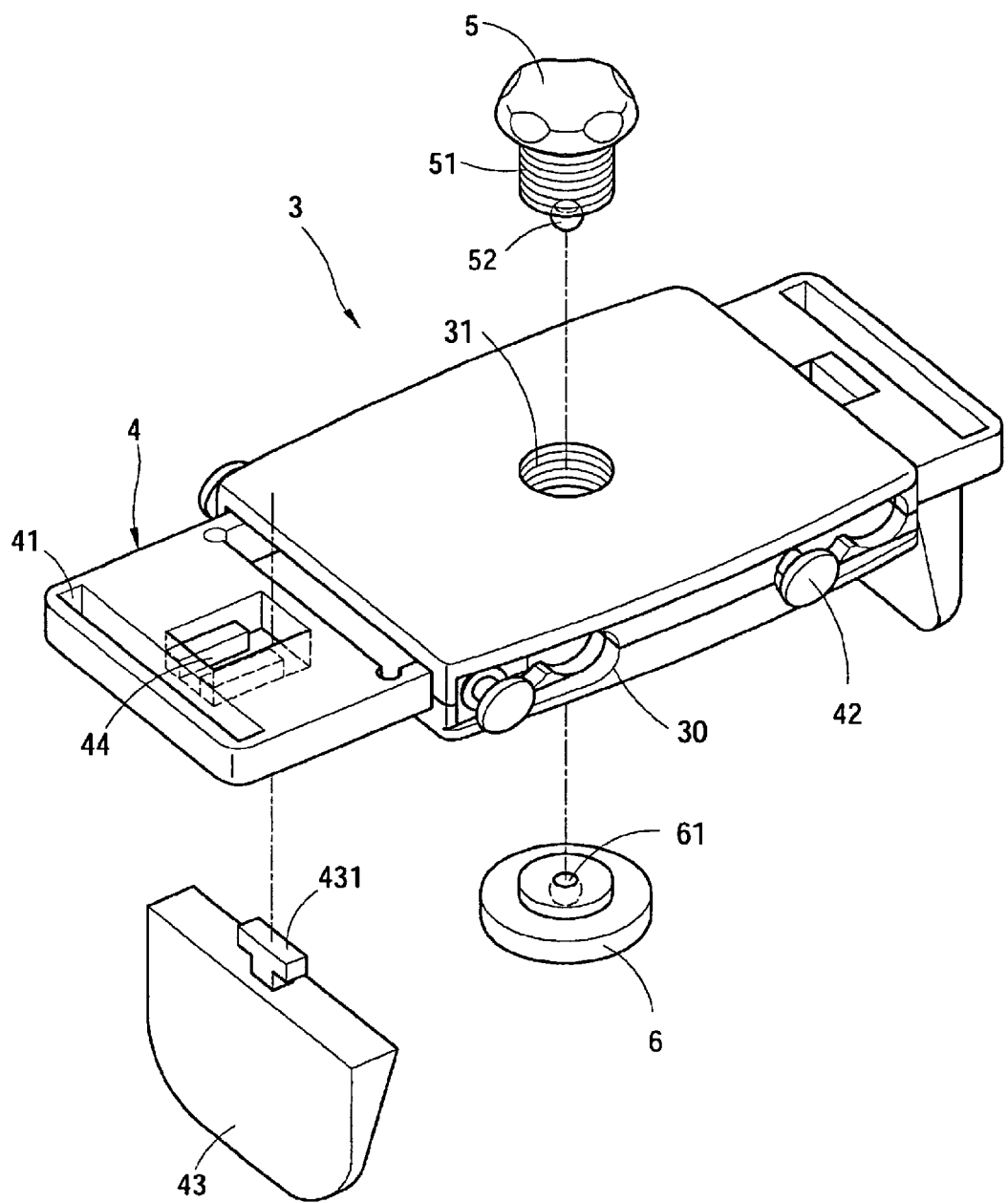
FIG. 3 is an illustrative diagram of the disassembled structure according to a preferred embodiment of the present invention.

Please refer to FIG. 3. The knob 5 on its side has an outer thread 51, and the finger pressing component 3 has an inner thread 31. The knob 5 is rotated for making vertical adjustment. When it is necessary to add pressure, the knob 5 is rotated downward, and the knob 5 exerts pressure onto a spacer 6. A coupling section 52 is disposed at the bottom of the knob 5, and the spacer 6 is designed as a coupling groove 61 corresponsive to the coupling section 52 of the knob 5. The spacer 6 will not rotate when the knob 5 is rotating, and thus will not produce a tugging action on the skin that will cause discomforts to the patient. The spacer 6 will only ascend or descend with the knob 5 accordingly, and the knob 5 will exert a pressure on the spacer 6. If the pressure is too large, the user can rotate the knob 5 upward to reduce the pressure on the spacer 6 and carry the spacer 6 upward. The oval plates 43 on both sides are coupled with the fixture 4.

Figure 4B:
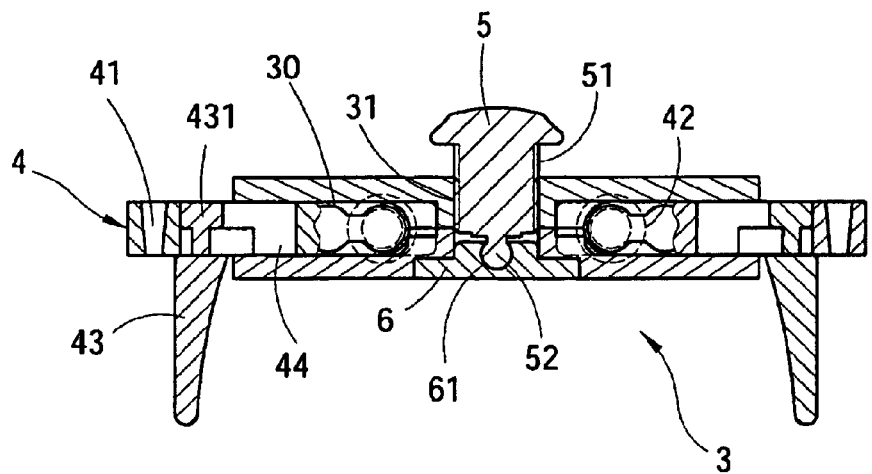
FIG. 4B is a diagram of the movement made by the present invention as shown in FIG. 4A.
Figure 4A:
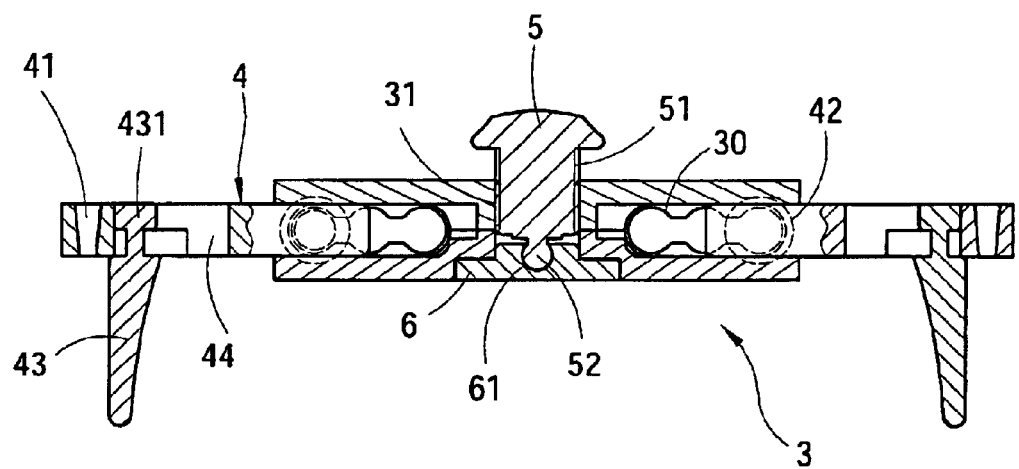
FIG. 4A is a cross-sectional diagram of section A—A of FIG. 2.

Please refer to FIGS. 2, 4A, and 4B. The rear ends 41 of the fixture 4 on both sides of the finger pressing component 3 are respectively coupled to the elastic bandage 1, and the finger pressing component 3 is coupled to the pivotal coupling end 42. When the elastic bandage 1 reaches a fixed position, a fine tune can be made by adjusting the fixtures 4 on both sides, such that the oval plates 43 on both sides can be fixed on the limb and thus improving the fixing of the tourniquet. If the patient 5 limb is too fat or this device is applied on the patient's body, the user can remove the oval plates 43 on both sides.

Figure 5B:
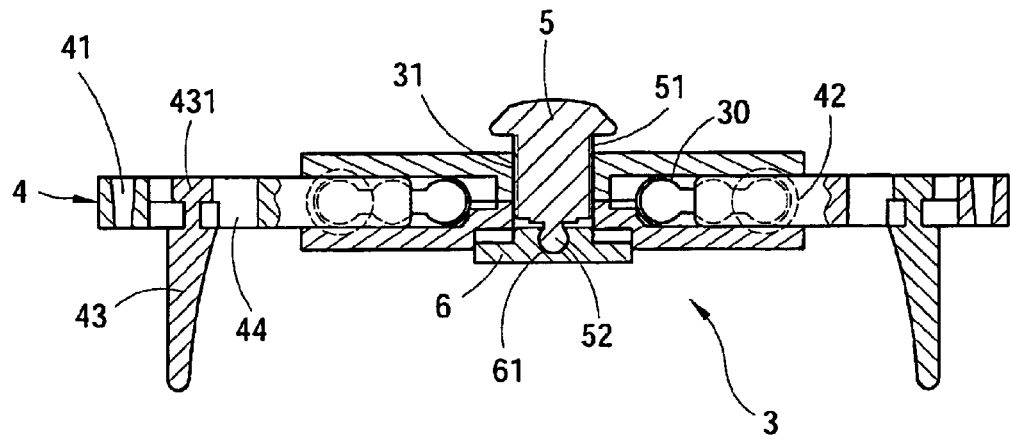
FIG. 5B is a diagram of the movement made by the present invention as shown in FIG. 5A.
Figure 5A:
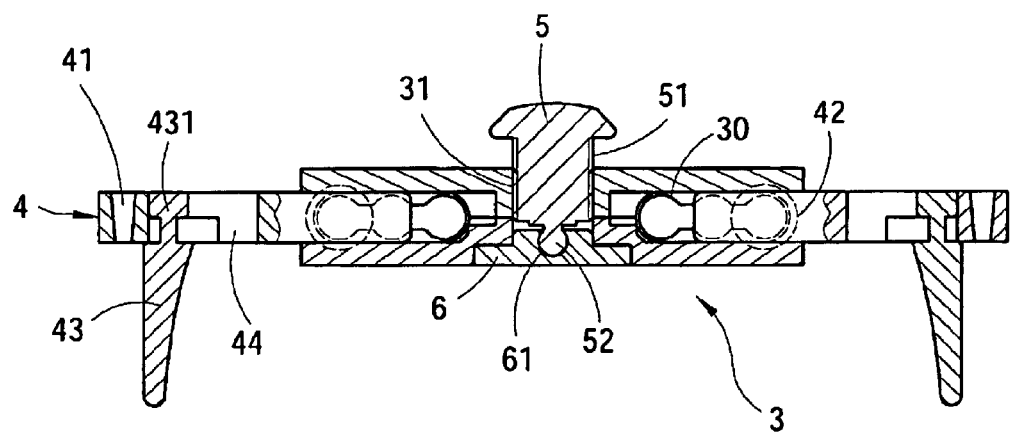
FIG. 5A is an illustrative diagram of the fine-tune knob and the fixture according to the present invention.

Please refer to FIGS. 5A and 5B. When the tourniquet is used on a patient, and the tourniquet is adjusted to a fixed position, the fixtures 4 on both sides are also adjusted to an appropriate position. When medical staffs need to add pressure, they may use the adjusting knob 5 to make the adjustment by rotating the knob 5 downward. The knob 5 will exert pressure onto the spacer 6. If the pressure is too large, the knob 5 can be rotated upward to reduce the pressure of the spacer 6, so that the knob 6 exerts pressure onto the spacer 6 directly instead of tugging the skin which will cause discomforts to the patient.

Figure 6:
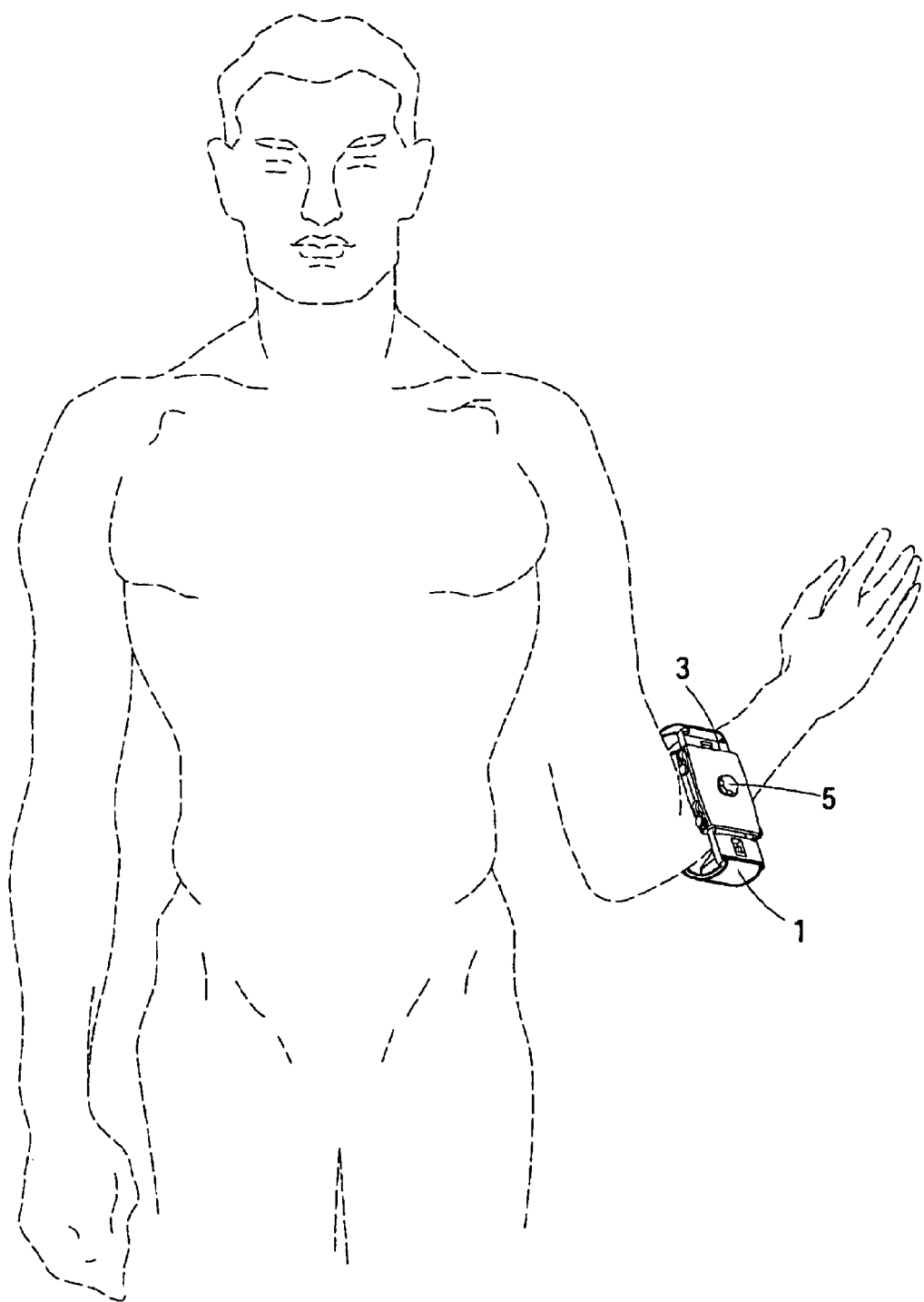
FIG. 6 is an illustrative diagram of the appearance of a preferred embodiment of the present invention.

Please refer to FIGS. 3 and 6. When the tourniquet is applied and fixed on a patient's limb, the distance between the fixtures 3 on both sides can be adjusted according to the size of the limb by rotating the knob 5 to exert an appropriate pressure onto the spacer 6 and improve the fixing of the tourniquet onto the limb.

What is claimed is:

1. A controllable tourniquet, comprising:

an elastic bandage;

a latch; and a finger pressing component; a fixture respectively coupled to both ends of said finger pressing component; an end of said fixture being a pivotal coupling end, and said pivotal coupling end being coupled to said finger pressing component; said fixture having a square latch groove and a latch section of an oval plate being coupled thereon, and the position of said latch section of the oval plate being adjusted in said latch groove; another end of said fixture being a rear end coupled to said elastic bandage, and said rear end being coupled to said elastic bandage; a knob being disposed at the top of said finger pressing component for exerting pressure onto a spacer by rotation; a plurality of grooves disposed on both sides of said finger pressing component for adjusting the position of said fixture and the tightness of the tourniquet.

2. The controllable tourniquet of claim 1, wherein said knob is rotated to adjust the pressure on said spacer and drive said spacer to exert pressure onto the skin.

3. The controllable tourniquet of claim 1, wherein said knob is coupled with said spacer by a coupling groove and a coupling section.

4. The controllable tourniquet of claim 1, wherein said fixtures on both sides of said finger pressing component are capable of adjusting the position of said pivotal coupling end to the position of the groove on said finger pressing component depending on the size of the patient's limb.

5. The controllable tourniquet of claim 1, wherein said knob comprises an outer thread, and said finger compressing component comprises an inner thread for precisely securing and adding pressure to said knob.

* * * * *